United States Patent
Bowden et al.

(10) Patent No.: US 8,663,286 B2
(45) Date of Patent: *Mar. 4, 2014

(54) COMPLIANT DYNAMIC SPINAL IMPLANT AND ASSOCIATED METHODS

(75) Inventors: Anton E. Bowden, Lindon, UT (US); Larry L. Howell, Orem, UT (US); Peter A. Halverson, Alpine, UT (US); Eric M. Stratton, Provo, UT (US)

(73) Assignee: Brigham Young University, Provo, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/709,240

(22) Filed: Feb. 19, 2010

(65) Prior Publication Data

US 2010/0211106 A1    Aug. 19, 2010

Related U.S. Application Data

(60) Provisional application No. 61/208,018, filed on Feb. 19, 2009, provisional application No. 61/210,740, filed on Mar. 19, 2009.

(51) Int. Cl.
*A61B 17/70* (2006.01)
*A61B 17/88* (2006.01)

(52) U.S. Cl.
USPC ............................ 606/260; 606/279

(58) Field of Classification Search
USPC ................ 606/279, 260, 246, 247, 257; 623/17.11–17.16; 128/898
See application file for complete search history.

(56) References Cited

U.S. PATENT DOCUMENTS

| | | |
|---|---|---|
| 3,945,053 A | 3/1976 | Hilberry et al. |
| 5,405,408 A | 4/1995 | Pitkin |
| 5,415,661 A | 5/1995 | Holmes |
| 5,772,661 A | 6/1998 | Michelson |
| 6,045,552 A | 4/2000 | Zucherman et al. |
| 6,379,354 B1 | 4/2002 | Rogozinski |
| 6,440,169 B1 | 8/2002 | Elberg et al. |
| 6,527,804 B1 | 3/2003 | Gauchet et al. |
| 6,540,785 B1 | 4/2003 | Gill et al. |
| 6,572,653 B1 | 6/2003 | Simonson |
| 6,579,320 B1 | 6/2003 | Gauchet et al. |
| 6,610,093 B1 | 8/2003 | Pisharodi |

(Continued)

FOREIGN PATENT DOCUMENTS

| | | |
|---|---|---|
| KR | 1020050080493 | 8/2005 |
| KR | 1020060113318 | 11/2006 |

(Continued)

OTHER PUBLICATIONS

U.S. Appl. No. 11/952,709, filed Dec. 7, 2007; Michael D. Ensign; office action mailed Mar. 17, 2011.

(Continued)

*Primary Examiner* — Pedro Philogene
(74) *Attorney, Agent, or Firm* — Thorpe North & Western LLP

(57) ABSTRACT

A spinal implant comprises a plurality of contiguous segments, said plurality of contiguous segments configured to apply a torque to a degenerate spinal segment in any of three orthogonal axes. At least one mounting connection is configured to connect said spinal implant to a mounting mechanism, said mounting mechanism being configured to attach said spinal implant to said degenerate spinal segment.

29 Claims, 14 Drawing Sheets

(56) References Cited

U.S. PATENT DOCUMENTS

| | | |
|---|---|---|
| 6,645,248 B2 | 11/2003 | Casutt |
| 6,723,127 B2 | 4/2004 | Ralph et al. |
| 6,793,678 B2 | 9/2004 | Hawkins |
| 6,802,867 B2 | 10/2004 | Manasas et al. |
| 6,811,567 B2 | 11/2004 | Reiley |
| 6,863,688 B2 | 3/2005 | Ralph et al. |
| 6,936,071 B1 | 8/2005 | Marnay et al. |
| 6,949,123 B2 | 9/2005 | Reiley |
| 6,964,666 B2 | 11/2005 | Jackson |
| 6,966,910 B2 * | 11/2005 | Ritland .................... 606/257 |
| 6,974,478 B2 | 12/2005 | Reiley et al. |
| 6,983,924 B2 | 1/2006 | Howell et al. |
| 6,991,632 B2 | 1/2006 | Ritland |
| 6,997,955 B2 | 2/2006 | Zubok et al. |
| 7,029,475 B2 | 4/2006 | Panjabi |
| 7,074,238 B2 | 7/2006 | Stinson et al. |
| 7,093,827 B2 | 8/2006 | Culpepper |
| 7,115,129 B2 | 10/2006 | Heggeness |
| 7,144,396 B2 | 12/2006 | Shluzas |
| 7,207,992 B2 | 4/2007 | Ritland |
| 7,229,441 B2 | 6/2007 | Trieu et al. |
| 7,326,210 B2 | 2/2008 | Jahng et al. |
| 7,338,398 B2 | 3/2008 | Whiting et al. |
| 7,361,196 B2 | 4/2008 | Fallin et al. |
| 7,371,238 B2 | 5/2008 | Soboleski et al. |
| 7,377,942 B2 | 5/2008 | Berry |
| 7,445,635 B2 | 11/2008 | Fallin et al. |
| 7,458,981 B2 | 12/2008 | Fielding et al. |
| 7,476,238 B2 * | 1/2009 | Panjabi .................... 606/257 |
| 7,476,251 B2 | 1/2009 | Zucherman et al. |
| 7,481,830 B2 | 1/2009 | Wall et al. |
| 7,485,133 B2 | 2/2009 | Cannon et al. |
| 7,485,134 B2 | 2/2009 | Simonson |
| 7,485,146 B1 | 2/2009 | Crook et al. |
| 7,491,218 B2 | 2/2009 | Landry et al. |
| 7,491,238 B2 | 2/2009 | Arnin et al. |
| 7,491,240 B1 | 2/2009 | Carver et al. |
| 7,494,507 B2 | 2/2009 | Dixon et al. |
| 7,537,615 B2 | 5/2009 | Lemaire |
| 7,618,441 B2 * | 11/2009 | Groiso .................... 606/248 |
| 7,632,292 B2 * | 12/2009 | Sengupta et al. ........ 606/257 |
| 7,682,375 B2 * | 3/2010 | Ritland .................... 606/247 |
| 7,785,351 B2 * | 8/2010 | Gordon et al. ........... 606/259 |
| 7,909,877 B2 | 3/2011 | Krueger et al. |
| 8,025,681 B2 | 9/2011 | Colleran et al. |
| 2002/0138077 A1 | 9/2002 | Ferree |
| 2003/0171751 A1 | 9/2003 | Ritland |
| 2004/0002708 A1 | 1/2004 | Ritland |
| 2004/0176849 A1 | 9/2004 | Zubok et al. |
| 2005/0101954 A1 | 5/2005 | Simonson |
| 2005/0113924 A1 | 5/2005 | Butterman |
| 2005/0113927 A1 | 5/2005 | Malek |
| 2005/0125065 A1 | 6/2005 | Zucherman et al. |
| 2005/0149023 A1 | 7/2005 | Ritland |
| 2005/0159818 A1 | 7/2005 | Blain |
| 2005/0165487 A1 | 7/2005 | Muhanna |
| 2005/0177156 A1 | 8/2005 | Timm et al. |
| 2005/0240270 A1 | 10/2005 | Zubok et al. |
| 2005/0261772 A1 | 11/2005 | Filippi et al. |
| 2006/0009768 A1 | 1/2006 | Ritland |
| 2006/0009850 A1 | 1/2006 | Frigg et al. |
| 2006/0036240 A1 | 2/2006 | Colleran et al. |
| 2006/0041314 A1 | 2/2006 | Millard |
| 2006/0052784 A1 | 3/2006 | Dant et al. |
| 2006/0084987 A1 | 4/2006 | Kim |
| 2006/0190079 A1 | 8/2006 | Istephanous et al. |
| 2006/0229609 A1 | 10/2006 | Wang |
| 2006/0240533 A1 | 10/2006 | Sengupta et al. |
| 2006/0271051 A1 | 11/2006 | Berrevoets |
| 2007/0016193 A1 | 1/2007 | Ritland |
| 2007/0028714 A1 | 2/2007 | Lusk et al. |
| 2007/0043365 A1 | 2/2007 | Ritland |
| 2007/0049936 A1 * | 3/2007 | Colleran et al. ........ 606/61 |
| 2007/0088440 A1 | 4/2007 | Eisermann et al. |
| 2007/0179618 A1 | 8/2007 | Trieu et al. |
| 2008/0015588 A1 | 1/2008 | Hawkes |
| 2008/0077246 A1 | 3/2008 | Fehling et al. |
| 2008/0140075 A1 | 6/2008 | Ensign |
| 2008/0183209 A1 | 7/2008 | Robinson et al. |
| 2008/0195208 A1 | 8/2008 | Castellvi |
| 2008/0195213 A1 | 8/2008 | Halverson et al. |
| 2008/0312693 A1 | 12/2008 | Trautwein et al. |
| 2009/0005819 A1 | 1/2009 | Ben-Mokhtar et al. |
| 2009/0048631 A1 | 2/2009 | Bhatnagar et al. |
| 2009/0228045 A1 | 9/2009 | Hayes et al. |
| 2009/0259257 A1 | 10/2009 | Prevost |
| 2009/0270921 A1 | 10/2009 | Krause |
| 2010/0204732 A1 | 8/2010 | Aschmann et al. |
| 2010/0211106 A1 | 8/2010 | Bowden |
| 2010/0217324 A1 | 8/2010 | Bowden et al. |
| 2010/0217326 A1 | 8/2010 | Bowden et al. |
| 2010/0217334 A1 | 8/2010 | Hawkes |
| 2010/0222821 A1 | 9/2010 | Bowden et al. |
| 2010/0222823 A1 | 9/2010 | Bowden et al. |
| 2010/0241232 A1 | 9/2010 | Halverson et al. |

FOREIGN PATENT DOCUMENTS

| | | |
|---|---|---|
| WO | WO 2004/071344 | 8/2004 |
| WO | WO 2005/051243 | 6/2005 |
| WO | WO 2005/107654 | 11/2005 |
| WO | WO 2008/070840 | 6/2008 |
| WO | WO 2008/100891 | 8/2008 |
| WO | WO 2010/096621 | 8/2010 |
| WO | WO 2010/096829 | 8/2010 |
| WO | WO 2010/108010 | 9/2010 |

OTHER PUBLICATIONS

Jeanneau et al.; "A Compliant Rolling Contact Joint and it's Application in a 3-DOF Planar Parallel Mechanism with Kinematic Analysis"; Proceedings of DETC'04, ASME 2004 Design Engineering Technical Conferences and Computers and Information in Engineering Conference; Sep. 28-Oct. 2, 2004; Salt Lake City, Utah USA. DETC2004-57264, 2004by ASME.

Cannon et al.; "Compliant Rolling-Contact Element Mechanisms"; Proceedings of IDETC/CIE 2005, 2005 ASME Design Engineering Technical Conferences & Computers and Information in Engineering Conference, Sep. 24-28, 2005, 2005; Long Beach, California, USA; DETC2005-84073.

Halverson et al.; "Concepts for Achieving Multi-Stability in Compliant Rolling—Contact Elements"; Proceedings of IDETC/CIE 2007; ASME 2007 International Design Engineering Technical Conferences & Computers and Information in Engineering Conference; Sep. 24-28, 2007; Las Vegas, USA; DETC2007-34836.

Halverson et al.; Tension-Based Multi-Stable Compliant Rolling-Contact Elements'; 13th National Conference on Mechanisms and Machines (NaCoMM-2007); IISc, Bangalore, India; Dec. 12-13, 2007.

Jacobsen et al.; "Components for the design of Lamina Emergent Mechanism"; Proceedings of IMECE 2007, 2007 ASME International Mechanical Engineering Congress and Exposition; Nov. 10-16, 2007; Seattle, USA.

Jacobsen et al.; "Mechanism and Machine Theory"; Mechanism and Machine Theory; 2009; pp. 2098-2109; vol. 44; Elsevier.

Stratton et al.; Force-Displacement Model of the Flexsure™ Spinal Implant; Proceedings of the ASME 2010 International Design Engineering Technical Conferences and Computers and Information in Engineering Conference IDETC/CIE Aug. 15-18, 2010; Montreal, Quebec, Canada.

U.S. Appl. No. 12/916,110, filed Oct. 29, 2010; Spencer P. Magleby.

U.S. Appl. No. 11/952,709, filed Dec. 7, 2007; Michael D. Ensign; office action received Sep. 24, 2010.

PCT Application PCT/US2010/025101; filed Feb. 23, 2010; David Hawkes; ISR mailed Sep. 27, 2010.

PCT Application PCT/US2007/086803; filed Dec. 7, 2007; Michael D. Ensign; ISR mailed May 19, 2008.

PCT Application PCT/US2008/053661; filed Feb. 12, 2008; Peter Halverson; ISR mailed Jun. 5, 2008.

(56) References Cited

OTHER PUBLICATIONS

PCT Application PCT/US2010/024674; filed Feb. 19, 2010; Anton E. Bowden; ISR mailed Nov. 19, 2010.
PCT Application PCT/US2010/027826; filed Mar. 18, 2010; Peter A. Halverson; ISR mailed Jan. 17, 2011.
U.S. Appl. No. 12/709,240, filed Feb. 19, 2010; Anton E. Bowden; office action issued Aug. 29, 2011.
U.S. Appl. No. 12/709,243, filed Feb. 19, 2010; Anton E. Bowden; office action issued Sep. 1, 2011.
U.S. Appl. No. 12/709,248, filed Feb. 19, 2010; Anton E. Bowden; office action issued Sep. 13, 2011.
U.S. Appl. No. 12/709,255, filed Feb. 19, 2010; Anton E. Bowden; office action issued Sep. 15, 2011.
U.S. Appl. No. 12/029,046, filed Feb. 11, 2008; Peter Halverson; office action issued Sep. 22, 2011.
U.S. Appl. No. 12/709,246, filed Feb. 19, 2010; Anton E. Bowden; office action issued Sep. 1, 2011.
U.S. Appl. 12/916,110, filed Oct. 29, 2010; Spencer P. Magleby; office action issued Mar. 16, 2012.
U.S. Appl. No. 12/711,131, filed Feb. 23, 2010; David T. Hawkes; office action issued Jun. 4, 2012.
U.S. Appl. No. 12/029,046, filed Feb. 11, 2008; Peter Halverson; office action issued Apr. 20, 2012.
U.S. Appl. No. 12/916,110, filed Oct. 29, 2010; Spencer P. Magleby; office action issued Mar. 16, 2012.
U.S. Appl. 12/709,248, filed Feb. 19, 2010; Anton E. Bowden; Notice of Allowance issued Jan. 5, 2012.
U.S. Appl. No. 12/916,110, filed Oct. 29, 2012; Spencer P. Magleby; office action dated Dec. 14, 2012.
U.S. Appl. No. 12/711,131, filed Feb. 23, 2010; David T. Hawkes; office action dated Dec. 26, 2012.
PCT/US2012/041360; filed Jun. 7, 2012; Brigham Young University, et al.; search report dated Dec. 14, 2014.
U.S. Appl. No. 12/726,816, filed Mar. 18, 2010; Peter Halverson; office action issued Jan. 31, 2013.
PCT Application PCT/US2012/041360; filing date Jun. 7, 2012; Eric Dodgen; International Search Report mailed Dec. 14, 2012.

* cited by examiner

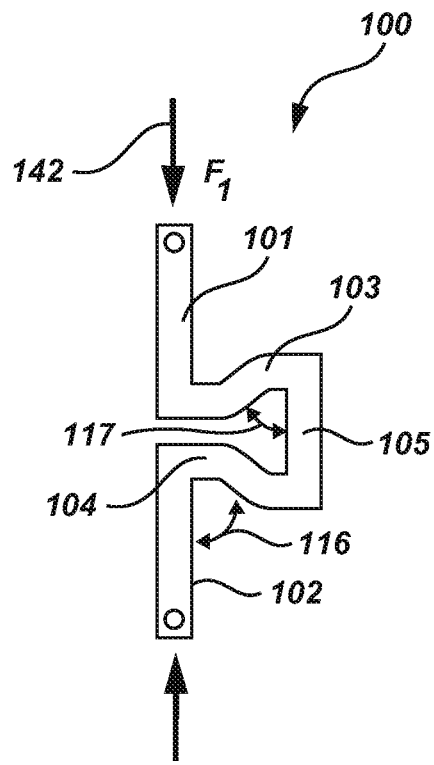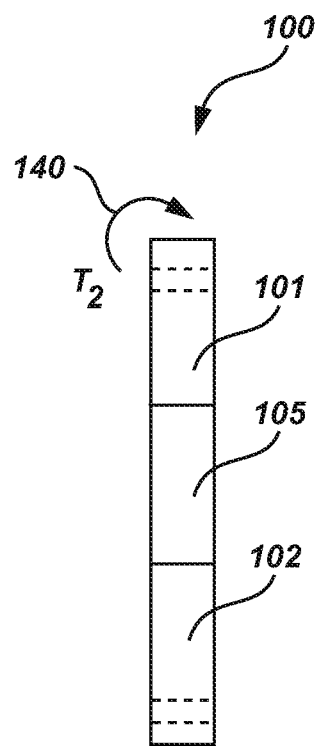
Fig. 14
Fig. 15

COMPLIANT DYNAMIC SPINAL IMPLANT AND ASSOCIATED METHODS

PRIORITY CLAIM

This application claims the benefit of and priority from U.S. Provisional Patent Application No. 61/208,018 filed on Feb. 19, 2009, and U.S. Provisional Patent Application No. 61/210,740 filed on Mar. 19, 2009, which are each incorporated herein in their entirety for all purposes by this reference.

STATEMENT REGARDING FEDERALLY SPONSORED RESEARCH

Research leading to this application was sponsored, in part, through National Science Foundation Award No. CMMI-0800606, "Lamina Emergent Mechanisms."

FIELD

Embodiments of the present invention relate generally to mechanical spinal implants and, more particularly, to dynamic spinal implants that relieve symptoms of degenerative spinal diseases, that restore healthy motion to an unhealthy spine, and that promote the healing of spinal tissues.

BACKGROUND

The human spine functions through a complex interaction of several parts of the anatomy. FIGS. 1 and 2 (the cross-section A-A of FIG. 1) illustrate a segment of the spine 4, with vertebra 5. The vertebra 5 include the vertebral body 6, the spinous process 8, transverse process 10, pedicle 12, and laminae 14. A functional spine, comprising several vertebra 5, typically subcategorized as being part of the cervical, thoracic, lumbar, sacral, and coccygeal regions as known, provides support to the head, neck, trunk, and transfer weight to lower limbs, protects the spinal cord 20, from which peripheral nerves 32 extend, and maintain the body in an upright position while sitting or standing.

Also illustrated in FIGS. 1 and 2, the spinal segment 4 includes intervertebral discs 20 that separate adjacent vertebra 5. The intervertebral discs 20 provide motion, load bearing and cushioning between adjacent vertebrae 5. Intervertebral discs 20 are the largest avascular structure in the body, relying on diffusion for its nutrition. The diffusion of nutrients is aided by the compression cycles that the intervertebral discs 20 undergo during the course of normal movement, which drives out waste products and cycles fluids. Lying down and resting reduces the load on the intervertebral discs 20 allowing nutrients to diffuse into the intervertebral discs 20.

Also illustrated in FIGS. 1 and 2, the spinal segment includes spinal facet joints 16. Spinal facet joints 16 join the adjacent vertebrae 6. The spinal facet joints 16 are synovial joints that function much like those of the fingers. Together with the intervertebral disc 20, the spinal facet joints 16 function to provide proper motion and stability to a spinal segment 4. Thus, each spinal segment 4 includes three joints: the intervertebral disc 20 in the anterior aspect of the spinal segment 4 and the two spinal facet joints 16 in the posterior aspect of the spinal segment 4.

For the spinal segment 4 to be healthy, each of the intervertebral disc 20 and the spinal facet joints 16 must be healthy. To remain healthy these joints require motion. The intervertebral disc 20 and the spinal facet joints 16 function together to provide both quality and quantity of motion. The quality of the motion is a exhibited by the non-linear energy storage (force-deflection, torque-rotation) behavior of the spinal segment 4. The quantity of motion is the range of segmental rotation and translation.

Back pain due to diseased, damaged, and/or degraded intervertebral discs 20 and/or spinal facet joints 16 is a significant health problem in the United States and globally. A non-exhaustive and non-limiting illustration of examples of diseased and/or damaged intervertebral discs are shown in FIG. 3. While a healthy intervertebral disc 20 is illustrated at the top of the spine segment 18, diseased and/or damaged discs are also illustrated. The diseased and/or damaged discs include a degenerated disc 22, a bulging disc 24, a herniated disc 25, a thinning disc 26, discs indicating symptoms of degeneration with osteophyte formation 28, as well as hypertrophic spinal facets 29.

A degenerating spinal segment 18 is believed to be the product of adverse changes to its biochemistry and biomechanics. These adverse changes create a degenerative cascade affecting the quality and/or quantity of motion and may ultimately lead to pain. For example, as the health of a spinal segment 18 degenerates and/or changes, the space through which the spinal cord 30 and peripheral nerves 32 (FIGS. 1 and 2) pass can become constricted and thereby impinge a nerve, causing pain. For example, the spinal cord 30 or peripheral nerves 32 may be contacted by a bulging disc 24 or herniated disc 25 or hypertrophic spinal facet 29 as illustrated in FIG. 3. As another example, a change in the spinal segment 18, such as by a thinning disc 26 may alter the way in which the disc functions, such that the disc and spinal facets may not provide the stability or motion required to reduce muscle, ligament, and tendon strain. In other words, the muscular system is required to compensate for the structural deficiency and/or instability of the diseased spinal segment 18, resulting in muscle fatigue, tissue strain, and hypertrophy of the spinal facets, further causing back pain. The pain this causes often leads patients to limit the pain-causing motion; but this limited motion, while offering temporary relief, may result in longer-term harm. because the lack of motion limits the ability of the disc to expel waste and obtain nutrients as discussed above.

Of course, other diseases of the disc and other back related problems and/or maladies afflict many people. For example, as the disc degenerates the spinal facet joints undergo a change in motion and in loading. This causes the spinal facet joints to begin to degenerate. Spinal facet joint arthritis is an additional source of pain. Also, scoliosis, or a lateral curvature of the spine, is illustrated in FIG. 4. A patient's body 40 is illustrated in outline. Also illustrated is the lateral curvature of a scoliotic spine 42 that is afflicted with scoliosis. The scoliotic center line 44 of the scoliotic spine 42 is illustrated, as compared to a healthy centerline or axis 46 of a healthy spinal column or functional spine unit. Conditions such as kyphosis, an exaggerated outward-posterior curvature of the thoracic region of the spine resulting in a rounded upper back, lordosis, an exaggerated forward curvature of the lumbar and cervical regions of the spine, and other conditions also afflict some patients.

In many instances of degenerative disc disease, fusion of the vertebrae is the standard of care for surgical treatment, illustrated in FIG. 5. In the U.S. alone, approximately 349,000 spinal fusions are performed each year at an estimated cost of $20.2 billion. The number of lower back, or lumbar, fusions performed in the U.S. is expected to grow to approximately 5 million annually by the year 2030 as the population ages, an increase of 2,200%.

Spinal fusion aims to limit the movement of the vertebra that are unstable or causing a patient pain and/or other symptoms. Spinal fusion typically involves the removal of a diseased disc 50, illustrated in outline in FIG. 5. The removed disc 50 is replaced by one or more fusion cages 52, which are filled or surrounded by autograft bone that typically is harvested by excising one or more spinal facet joints 57. Vertebral bodies 51 adjacent the removed disc 50 are stabilized with one or more posterior supports 58 that are fixedly connected to the vertebral bodies 51 with the use of pedicle screws 54 that are screwed—such as by use of a bolt-style head 56 to turn the pedicle screw 54—into a hole drilled into the pedicle 12 of the vertebral bodies 51.

Fusion, however, often fails to provide adequate or sufficient long-term relief in about one-half of the treatments, resulting in low patient satisfaction. Further, fusion, by definition, restricts the overall motion of the treated functional spine unit, imposing increased stresses and range of motion on those portions of the spinal segment adjacent to the fused vertebral bodies 51. Fusion of a spinal segment has been indicated as a potential cause of degeneration to segments adjacent to the fusion. The adjacent spinal facet joints 57 and adjacent discs 59 often have to bear a greater load as a result of the fusion than would typically be the case, leading to possible overloading and, in turn, degeneration. Thus, surgical fusion often provides short-term relief, but possibly greater long-term spinal degradation than would otherwise have occurred.

Thus, a challenge to alleviating the back pain associated with various ailments is to find a remedy that, ideally, does not involve removing the diseased disc or damaging the spinal facet joints, and that provides sufficient stability to the diseased segment to alleviate pain and/or other symptoms, while still providing sufficient freedom of movement to allow the disc and spinal facet joints to return to health.

A further challenge is simply the complex, multi-dimensional nature of movement associated with a functional spine unit. Illustrated in FIG. 6 are the varying, orthogonal axes around which a functional spine unit moves. For example, a vertebra 5 is illustrated with an X-axis 60, around which a forward bending motion, or flexion 61 in the anterior direction occurs. Flexion 61 is the motion that occurs when a person bends forward, for example. A rearward bending motion, or extension, 62 is also illustrated. The Y-axis 63 is the axis around which lateral extension, or bending, 64, left and right, occurs. The Z-axis 65 is the axis around which axial rotation 66, left and right, occurs. Spinal fusion, as discussed above, limits or prevents flexion 61-extension 62, but also limits or prevents motion in lateral extension, or bending, 64 and axial rotation 66. Thus, an improved alternative remedy to fusion preferably allows for movement with improved stability around each of the three axes, 60, 63, and 65.

Another difficulty associated with the complex motion of the spine is that the center-of-rotation for movement around each of the X-axis 60, Y-axis 63, and Z-axis 65 differs for each axis. This is illustrated in FIG. 7, in which the center-of-rotation for the flexion 61-extension 62 motion around the X-axis 60 is located at flexion-extension center-of-rotation 70. The center-of-rotation for the lateral extension, or bending, 64 motion around the Y-axis 63 is located at lateral extension, or bending, center-of-rotation 73. The center-of-rotation for the axial rotation 66 around the Z-axis 65 is located at axial rotation center-of-rotation 75. For more complex motion patterns (e.g., combined flexion, lateral extension/bending, etc.) a two-dimensional representation of the center-of-rotation is inadequate, but the three-dimensional equivalent called the helical axis of motion, or instantaneous screw axis can be employed. Spinal remedies which force rotation of a spinal segment around any axis other than the natural helical axis impose additional stresses on the tissue structures at both the diseased spinal segments and the adjacent spinal segments. Compounding the issue for the centers-of-rotation is that they actually change location during the movement, i.e., the location of the centers-of-rotation are instantaneous. Thus, a preferable remedy to spinal problems would account for the different instantaneous centers-of-rotation throughout the range of motion. Stated differently, a preferable remedy to spinal problems would allow the diseased spinal segment and adjacent spinal segments to under motion approximate that of the natural helical axis through the range of motions.

Many previous efforts have been made to solve at least some of the problems associated with spinal fusion, but with varying degrees of success. For example, U.S. Pat. No. 7,632,292 (the '292 patent) to Sengupta and Mulholland, discloses an arched-shaped spring mechanism that is attached to adjacent vertebrae via pedicle screws. This device relies on the extension and compression of the spring to accommodate flexion 61 and extension 62 about the X-axis 60 illustrated in FIG. 6. The device disclosed in the '292 patent addresses only flexion-extension and neither lateral extension/bending nor axial rotation, which would both still be improperly supported. Further, the '292 patent does not account for the instantaneous centers-of-rotation; in other words, the centers-of-rotation will be misplaced for motions other than flexion. In addition, it may be anticipated that the device is either too stiff to provide proper motion or that the extension-compression cycles may lead to fatigue failure of the device.

Another example is U.S. Pat. No. 6,966,910 (the '910 patent) and its associated family of applications to Ritland. As with the '292 patent, the '910 patent relies on the extension-compression cycle of a spring mechanism—specifically the reverse curves within the mechanism—to accommodate flexion 61 and extension 62 about the X-axis 60 illustrated in FIG. 6. Lateral extension/bending and axial rotation are not addressed.

Thus, there exists a need for a spinal implant that protects the spinal cord and the peripheral nerves from damage.

Further, there exists a need for a spinal implant that reduces the stress on a diseased and/or damaged disc without overloading the adjacent discs and vertebrae that could initiate progressive degeneration or diseases in the adjacent discs and vertebrae.

Another need exists for a spinal implant that minimizes or avoids wear. Previous spinal implants that have parts that move against each other may cause wear particles or debris—i.e., small pieces of the implant—to come free, potentially loosening the implant and/or decreasing the stability of the implant, and/or potentially causing adjacent bone or tissue to degrade because of contamination. Further, wear particles may change the chemical structure and/or chemical stability of biocompatible devices such that the resultant chemical structure and/or chemical stability becomes non-biocompatible or causes the implant to degrade at an accelerated rate.

A need also exists for a spinal implant that provides for proper force-deflection behavior of the spinal implant (kinetics)—as noted above in the discussion of FIG. 6—preferably to approximate those of a normal, functional spine unit to relieve the load and strain on the intervertebral discs, to protect the spinal facet joints, to reduce the risk of damage to segments of the spine adjacent to the diseased segment, to reduce muscle fatigue and reduce and/or eliminate subsequent pain.

A need also exists for a spinal implant that exhibits kinematics—such as the limits of the ranges-of-motion and the centers-of-rotation noted above in the discussion of FIG. 7—that, preferably, are maintained near those of a functional spine unit to maintain an effective range of motion for the intervertebral discs, spinal facet joints, muscles, ligaments, and the tendons around the spine and to reduce the amount of neural element strain, e.g., the strain on the spinal cord and/or other parts of the nervous system.

A need still exists for a spinal implant that relieves a portion of the load that would otherwise be borne by the diseased disc. In addition, a compliant spinal implant preferably distracts (or extends) the space—including the space anteriorly and/or posteriorly—between the vertebrae adjacent to the diseased discs.

In addition, a need exists for a spinal implant that preferably restores a torque-rotation signature near that of a healthy, functional spine unit.

Spinal implants including one or more of the recited features and benefits could improve the opportunity for the diseased spinal segment and/or intervertebral discs and/or spinal facet joints to heal.

SUMMARY

Various features and embodiments of the invention disclosed herein have been the subject of substantial ongoing experimentation and have shown a significant improvement over the prior art. Among other improvements, the embodiments of the invention provide robust and durable compliant spinal implants that have a smaller profile and accommodate motion in three axes as compared to a single axis of motion of the prior art. It is believed that the embodiments, collectively and/or individually, represent an unexpected advance in the field and will enable physicians to provide spinal implants that can be selected and individually adjusted pre-operatively, intra-operatively (i.e., during the operation), and post-operatively to restore the normal or near normal function of a damaged or diseased spinal segment.

Embodiments of the compliant dynamic spinal implant include a geometry that, once implanted, is configured to allow flexion-extension, and/or lateral extension/bending, and/or axial rotation with an instantaneous or near-instantaneous centers-of-rotation for the diseased and/or damaged disc and adjacent vertebrae that are similar to that of a healthy spinal segment. Thus, the implant restores, to a degree, close to normal movement of the diseased and/or damaged discs and adjacent vertebrae, which, in turn, promotes healing of the diseased and/or damaged disc.

Other embodiments of the spinal implant provide protection to the spine, discs, spinal cord, and peripheral nerves by reducing the risk of harmful, damaging, and/or painful movements while still providing a sufficient range of motion to promote healing and while reducing the risk of damage and/or disease to adjacent discs and vertebrae. Embodiments of the spinal implant do so by reducing the stresses on a diseased and/or damaged spinal segment without overloading the adjacent spinal segments, including the adjacent intervertebral discs, spinal facet joints, and vertebrae, that could initiate progressive degeneration or diseases in the adjacent spinal segments. For example, embodiments of a spinal implant preferably relieve a portion of the compressive load that would otherwise be borne by the diseased disc and, preferably, distracts (or increases) the space between the vertebrae adjacent to the diseased discs, which improves the opportunity for the diseased disc to heal.

Embodiments of the spinal implant preferably provide for force-deflection behaviors near those of a normal, functional spine unit—such as the healthy discs and/or spinal facet joints near the damaged and/or diseased spinal segments of a patient—to reduce muscle fatigue and subsequent pain. Additionally, embodiments of the spinal implant preferably provide proper motion—such as the centers-of-rotation, whether instantaneous or otherwise, limits of the ranges-of-motion, and the types of motion—that are maintained near those of a functional spine unit to maintain an effective range of motion for the muscles and the tendons around the spine and to reduce the amount of spinal cord strain. For instance, embodiments of the compliant spinal implant preferably restore a torque-rotation signature near that of a healthy, functional spine unit.

Embodiments of the present invention exhibit reduced or limited wear compared to prior art devices. Such reduced wear is provided, preferably, by having few to no parts within the implant itself that move or wear against other parts of the spinal implant or against the vertebrae and/or other skeletal tissue that might cause the implant to wear. Thus, embodiments of the spinal implant produce few to no wear particles when compared to prior devices.

Further embodiments include spinal implants that have a geometry engineered and configured to provide one or more of the above benefits. Embodiments of the spinal implant include a first attachment on a first length and a second attachment on a second length. Each attachment is configured for connecting and attaching to a device (typically, although not necessarily, pedicle screws and other similar devices) for temporarily or permanently fixing the spinal implant to one or more vertebrae. The first length and the second length are joined by a third section having a geometry engineered to provide one or more of the above benefits. The spinal implant preferably relies upon the geometry and the material from which the implant is manufactured to provide torque to oppose the flexion-extension of the spine, rather than compression-extension as in prior art devices. In addition, the spinal implant preferably relies upon the geometry and the material from which the implant is manufactured to provide compression and extension to oppose the lateral extension/bending of the spine.

Embodiments of the spinal implant are preferably made of biocompatible materials, including, but not limited to, biocompatible polymers and plastics, bioabsorbable materials, stainless steel, titanium, nitinol, shape-memory materials and/or alloys, and other similar materials. Additionally, embodiments of the spinal implant can be manufactured with materials that provide for pre-operative, operative, and post-operative adjustment of the implant and the manner in which it responds to a given input such as stress and/or torque, and, in the instance of post-operative adjustment, preferably adjustment through minimally invasive techniques and, more preferably, through non-invasive techniques. Embodiments of methods of adjusting the spinal implant are also disclosed.

Embodiments of methods of implanting the spinal implant are also disclosed.

Methods of using the above described system to detect leaks are also disclosed.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Summary does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

To further clarify the above and other advantages and features of the one or more present inventions, reference to specific embodiments thereof are illustrated in the appended drawings. The drawings depict only exemplary embodiments and are therefore not to be considered limiting. One or more embodiments will be described and explained with additional specificity and detail through the use of the accompanying drawings in which:

FIG. 14 is a posterior view of the spinal implant of FIG. 8 undergoing a compressive load and a torsional load;

FIG. 15 is a lateral view of the spinal implant of FIG. 9 undergoing a compressive load and a torsional load;

The drawings are not necessarily to scale.

DETAILED DESCRIPTION

As noted above, the kinetics and kinematics of the spine are quite complex, involving three separate axes around which motion occurs and three separate centers-of-rotation for the different motions. Applicants have recognized that previous spinal implants often address just one form of motion, typically flexion and extension, often through the use of springs of some type that flex and compress. Efforts to address more than one mode of rotation or motion typically tend to be complex, large, and often do not address each individual motion as effectively as devices dedicated to a single motion.

Through significant experimentation and engineering work, Applicants have discovered geometries that rely, in part, on the concept of torsion, rather than primarily compression and extension of springs, to provide a seemingly simple, yet decidedly complex, geometry that accommodates motion and stiffness around the three axis and accommodates the separate centers-of-rotation for each motion (flexion-extension, lateral extension or bending, and axial rotation). A compliant mechanism gains its motion from the deflection of flexible, resilient members. Such devices move without the aid of traditional sliding joints and bearings, thus increasing precision and eliminating friction and wear. They also integrate spring and hinge functions, allowing for the design of desired force-deflection behavior.

Figure 8:
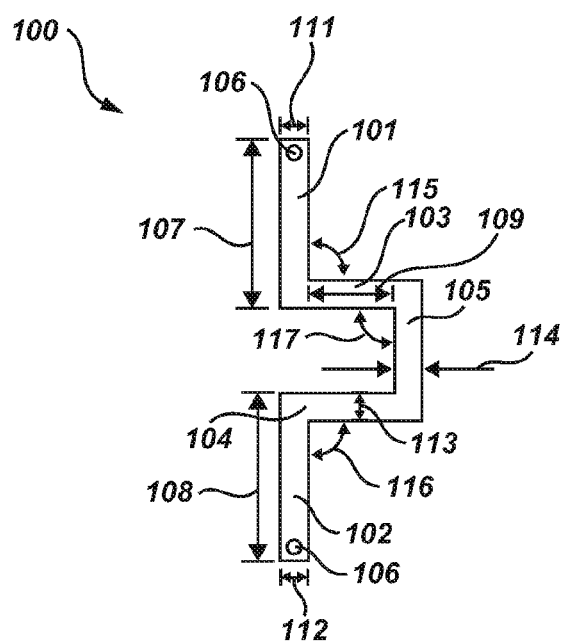
FIG. 8 illustrates an embodiment of an unimplanted compliant dynamic spinal implant, shown from the rear/posterior view, i.e., as it would appear from the rear of a person when implanted.
Figure 9:
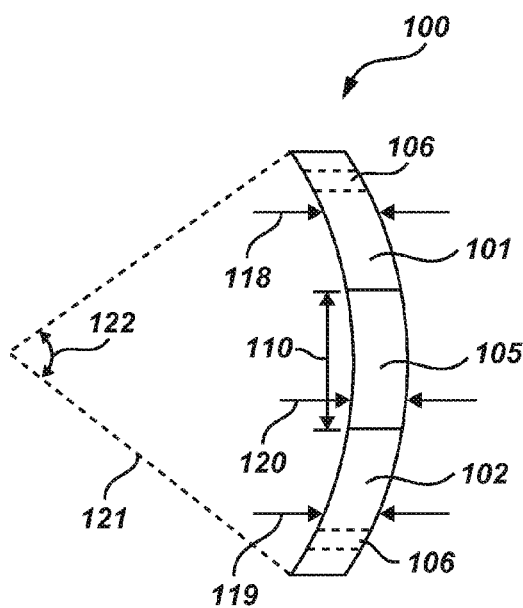
FIG. 9 is a lateral/side view of the spinal implant shown in FIG. 8.

An embodiment of a compliant dynamic spinal implant 100 is illustrated in FIGS. 8 and 9, which is an embodiment of a geometry that accomplishes, in part, the objectives provided above and in the background section. A posterior view of the spinal implant 100 is presented in FIG. 8—reference being made to the direction the spinal implant would be viewed from when implanted in a patient. In other words, the spinal implant 100 in FIG. 8 appears as it would as viewed it from the patient's back. A lateral, or side, view, of the implant is presented in FIG. 9. It will be understood that while these references to view are presented for clarity, it should be understood the spinal implants 100 shown in FIGS. 8 and 9 appear in their unstressed, pre-implant condition, as will be explained in further detail below. In this particular embodiment, the spinal implant 100 comprises a plurality of contiguous segments. In one embodiment, these contiguous segments include a first segment 101, having a first length 107, a first width 111, and a first height or thickness 118; a second segment 102 having a second length 108, a second width 112, and a second height or thickness 119; a third segment 103 having a third length 109, a third width, and a third height or thickness; a fourth segment 104 having a fourth length, a fourth width 113, and a fourth height or thickness. The spinal implant 100 also includes a fifth segment 105 having a fifth length 110, a fifth width 114, and a fifth height or thickness 120. Of course, one having skill in the art would understand that other geometries and configurations exist—including greater or fewer segments—that accomplish, in part, the recited objectives.

In this particular embodiment, the third width is the same width as the fourth width 113. Likewise, the fourth length is the same length as the third length 109. Furthermore, the heights of each segment discussed, including, the third and fourth heights, are the same as the first height 118, second height 119, and fifth height 120, respectively. Of course, the specific dimensions—including those not individually discussed—may be the same or they may differ from each other as one having skill in the art would understand.

As illustrated, the plurality of segments form angles at the location in which adjacent segments intersect. In other words, a plurality of angles exist, one angle for each intersection between two adjacent segments. For example, the first segment 101 is joined to the third segment 103, creating a first angle 115 between the first segment 101 and the third segment 103. The third segment 103 is joined to the fifth segment creating a second angle 117. The fifth segment 105 is, in turn, joined to the fourth segment 104, creating a third angle that, in this instance, is the same angle as the second angle 117. The fourth segment 104, in turn, is joined to the second segment 102, creating a fourth angle 116.

When reference is made to that the individual segments being "joined," it is understood that the segments may be temporarily joined, through a removable connection, such as bolts, screws, biocompatible adhesives, and the like. Alternatively, one or more of the segments may be joined permanently, such as through the use of biocompatible epoxies, polymers, and other known methods of joining the segments. In yet another embodiment, the individual segments may be formed as a single, unitary piece, such as by laminating, molding, pressing, stamping, milling, and other known methods.

In the embodiment illustrated, each of the angles 115, 116, and 117 are each right angles, thus forming a "U" configuration or shape of the contiguous segments, with each of the segments lying within proximately the same plane before implantation, although the measurement of each angle may differ from the others and fall within a variety of ranges. For example, the measurement of one or more of the angles may range from about 80° to about 100°; from about 70° to about 110°; and from about 45° to about 135°; and so forth.

As noted, embodiments of the spinal implant 100 use, in part, torsion to apply a force or load to the vertebrae of a patient. Typically, although not necessarily, the spinal implant 100 has an initial curvature to the device, as indicated in FIG. 9 by torsion angle 122 with a radius of curvature 121. FIG. 9, in the pre-implanted condition, includes this torsion angle 122, thus, as will be discussed below when explaining the procedure to implant the device, the spinal implant will provide a known or selected torque when it is straightened for implantation. Of course, the magnitude of this torque is a function of the radius of curvature 121, the material from which the spinal implant 100, is manufactured, and the specific geometry of each of the individual segments.

The spinal implant 100 optionally includes at least one mounting connection for connecting the spinal implant 100 to a mounting mechanism. For example, an embodiment of a mounting connection includes through holes 106 (FIG. 8), through which a mounting mechanism, typically, although not necessarily, pedicle screws, are positioned to hold the spinal implant in position in the patient—i.e., the mounting mechanism attaches the spinal implant 100 to at least a portion of a spinal segment, such as a vertebra, a pedicle, or other bony structure of a patient as will be discussed below. Of course, pedicle screws are merely one example of a mounting mechanism for attaching the spinal implant 100 to a patient's vertebrae. Other mounting mechanisms, such as the use of pins, biocompatible adhesives, straps, and the like, fall within the scope of this disclosure.

The spinal implant 100 can be formed of biocompatible plastics, polymers, metals, metal alloys, laminates, shape-memory materials, and other similar materials, either wholly as one material or as a combination of materials—i.e., different segments may be manufactured from different materials. Optionally, embodiments of the spinal implant can be made from bioabsorbable materials that a patient's body will naturally breakdown over time, thus potentially avoiding the need for a second surgery to remove the spinal implant 100, should such an option prove necessary and/or desirable.

An embodiment of the spinal implant 100 can optionally be made with nitinol, a metal alloy of nickel and titanium, that provides the ability of shape-memory. A spinal implant 100 made from such materials would be manufactured into a first shape or geometry or configuration (e.g., the length of the first and second segments 101 and 102, the radius of curvature 121, etc.) having a known and desired first torque response. The spinal implant 100 would then be manipulated into a second shape or geometry having a known and desired second torque response. The spinal implant 100, in the second shape or geometry or configuration, then would be implanted in the patient. After implantation, a physician can apply an activating agent, such as heat, current, or other parameter, to cause the spinal implant 100 to revert back to its original, first shape or geometry, allowing the material to consequently revert to its first torque response. Thus, a measure of adjustability in the torque response of the spinal implant 100—even post-surgery—can be manufactured into the spinal implant 100. For example, in the case of nitinol, applying a parameter such as heat to the spinal implant and, in so doing, raising the spinal implant to a temperature above the transition temperature of the nitinol causes the spinal implant to revert to its first shape or geometry. In so doing, the stiffness of the spinal implant could be altered by, for example, making the spinal implant significantly stiffer so that it approximates more closely the stiffness provided by a spinal fusion procedure.

Another embodiment of the spinal implant 100 can be made from bioabsorbable materials, as mentioned. The patient's body would slowly absorb the spinal implant 100 and, in the process of so doing, the compressive load or force and torque provided or born by the spinal implant 100 would slowly be transferred to the intervertebral discs and/or vertebrae of the patient as the patient's spine healed and/or improved in health and strength. Thus, a bioabsorbable device contemplates and allows for a patient to regain his or her spinal health, an adjustment and transfer of force and torque from the spinal implant to the patient's body, and the eventual removal of the spinal implant through absorption rather than surgery.

An advantage of embodiments of the spinal implants disclosed—provided that they are manufactured as single, unitary piece—is that they do not have any joints or surfaces that might rub or wear against each other because the embodiments rely on deflection of the segment(s) to provide a force and/or torque. The relative lack of rubbing or movement against other elements as compared to prior art devices minimizes or prevents the formation of wear particles that might otherwise be generated. This is the case for those prior art devices that have biocompatible surfaces that might wear off to expose non-biocompatible surfaces or, in some instances, the wear causes the biocompatible surface to become non-biocompatible, leading to additional wearing of the prior art devices at an accelerated rate.

Figure 10:
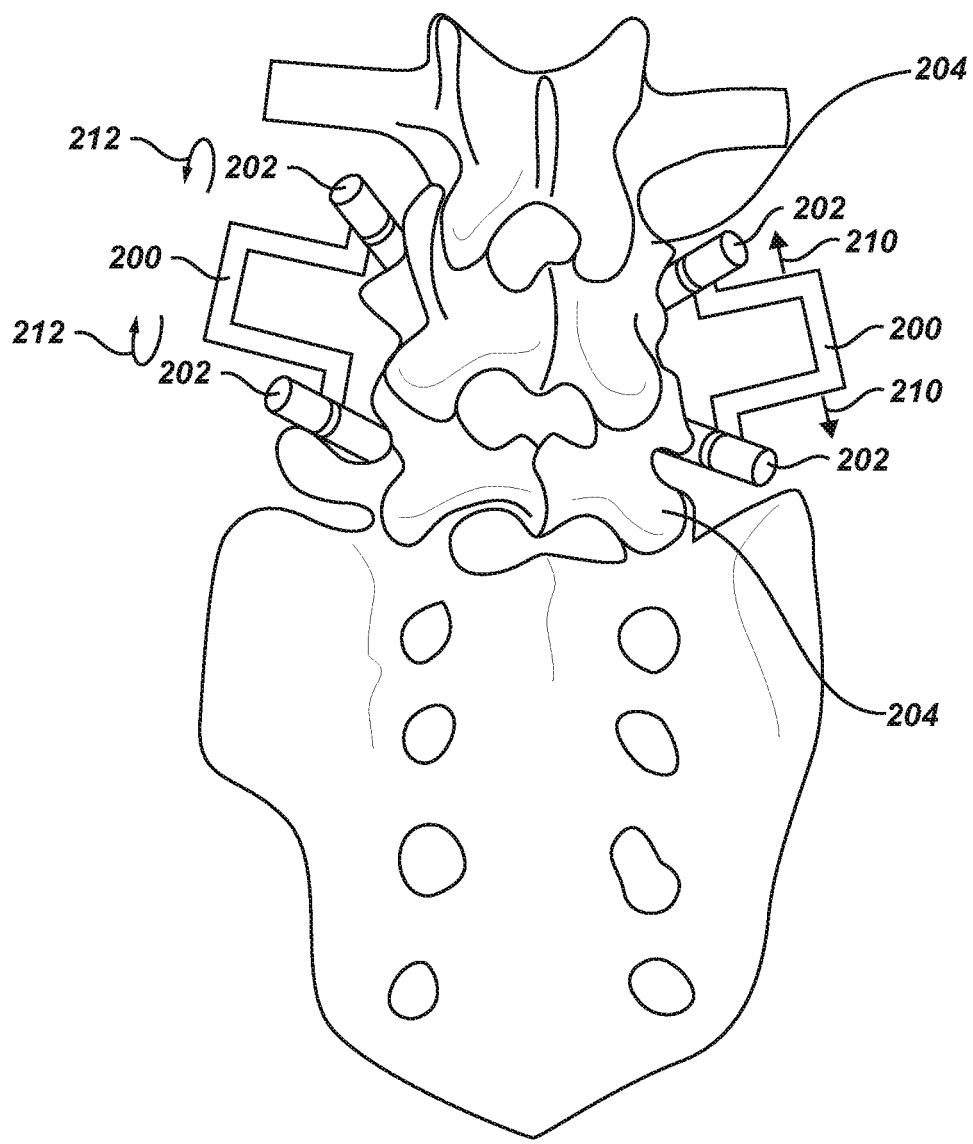
FIG. 10 shows embodiments of the spinal implant as they would appear implanted in a pair of lumbar vertebrae as viewed from the rear.
Figure 11:
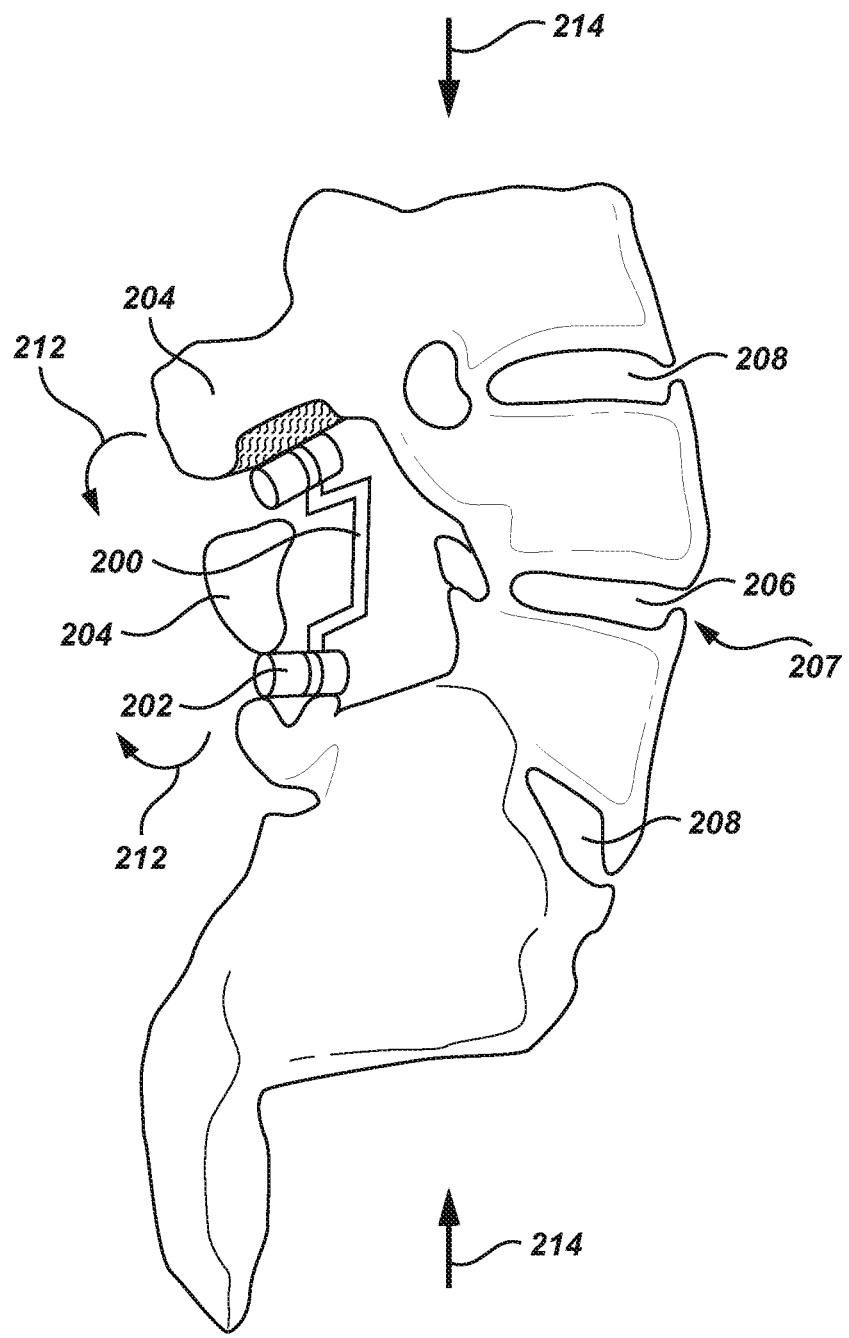
FIG. 11 is a lateral/side view of one of the spinal implants of FIG. 10.

For context, FIGS. 10 and 11 illustrate embodiments of the spinal implant 200 as they might appear implanted on a lumbar portion of the spine of a patient. The spinal implants 200 are fixed to the vertebrae 204 adjacent to a diseased disc 206. In this embodiment, pedicle screws 202 are used to fix the spinal implants 200 to the vertebrae 204. (The method of surgical implantation will be discussed in more detail below.) Once implanted, the spinal implants 200 optionally provide an extension force 210, if they are prestressed, as will be discussed below, to help distract the vertebrae 204 from the diseased disc 206. Alternatively, the spinal implants 200 resist a compressive force 214 from the normal action of gravity upon the person, thus supporting a portion of the load that would otherwise have been born by the diseased disc 206. In addition, the spinal implants provide a torque 212 (about an axis perpendicular to the page of FIG. 10) that distracts the diseased disc 206 and, preferably, distracts an anterior portion 207 of the diseased disc 206. The torque 212 applied by the spinal implants 200 can be selected and adjusted to compensate at least partially and, preferably, almost fully, for the diseased disc 206, as will be explained further below.

Figure 1:
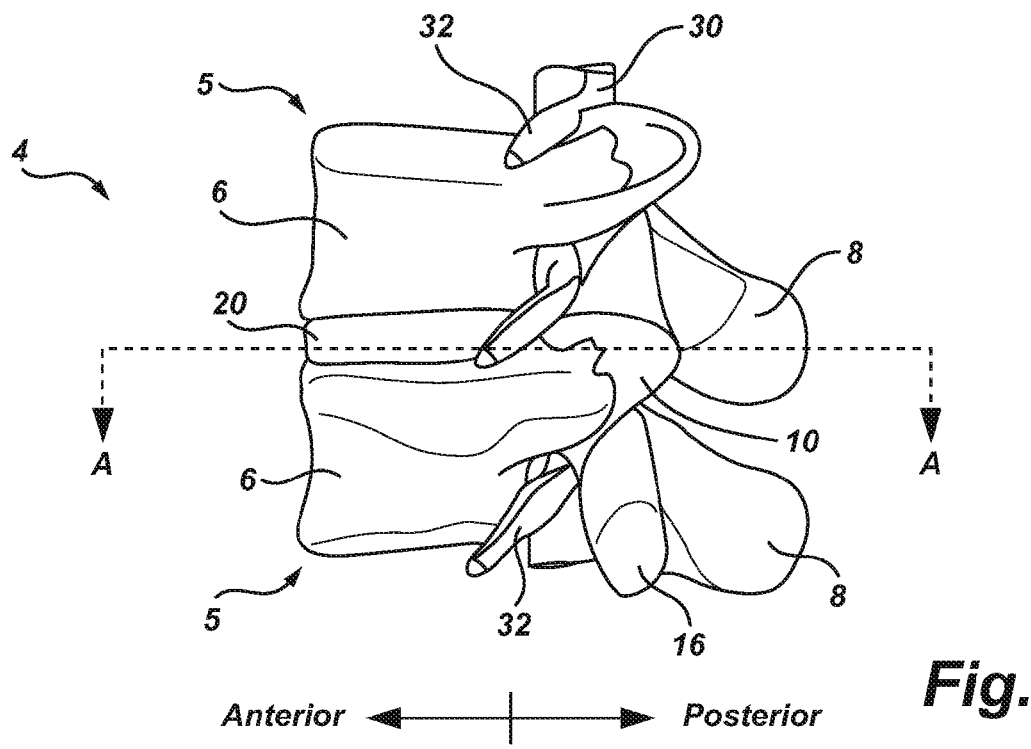
FIG. 1 is a segment of a functional spine unit.
Figure 2:
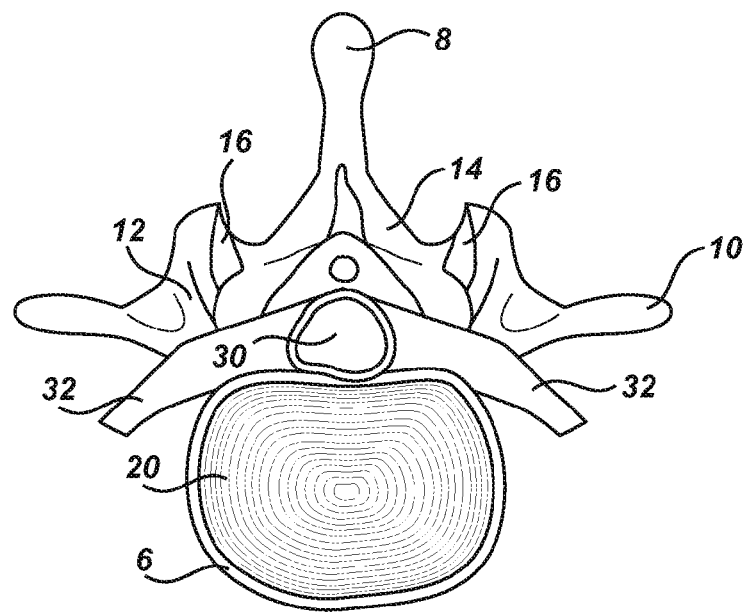
FIG. 2 is a cross-section of the segment of the functional spine unit illustrated in FIG. 1, taken along section A-A of FIG. 1.
Figure 3:
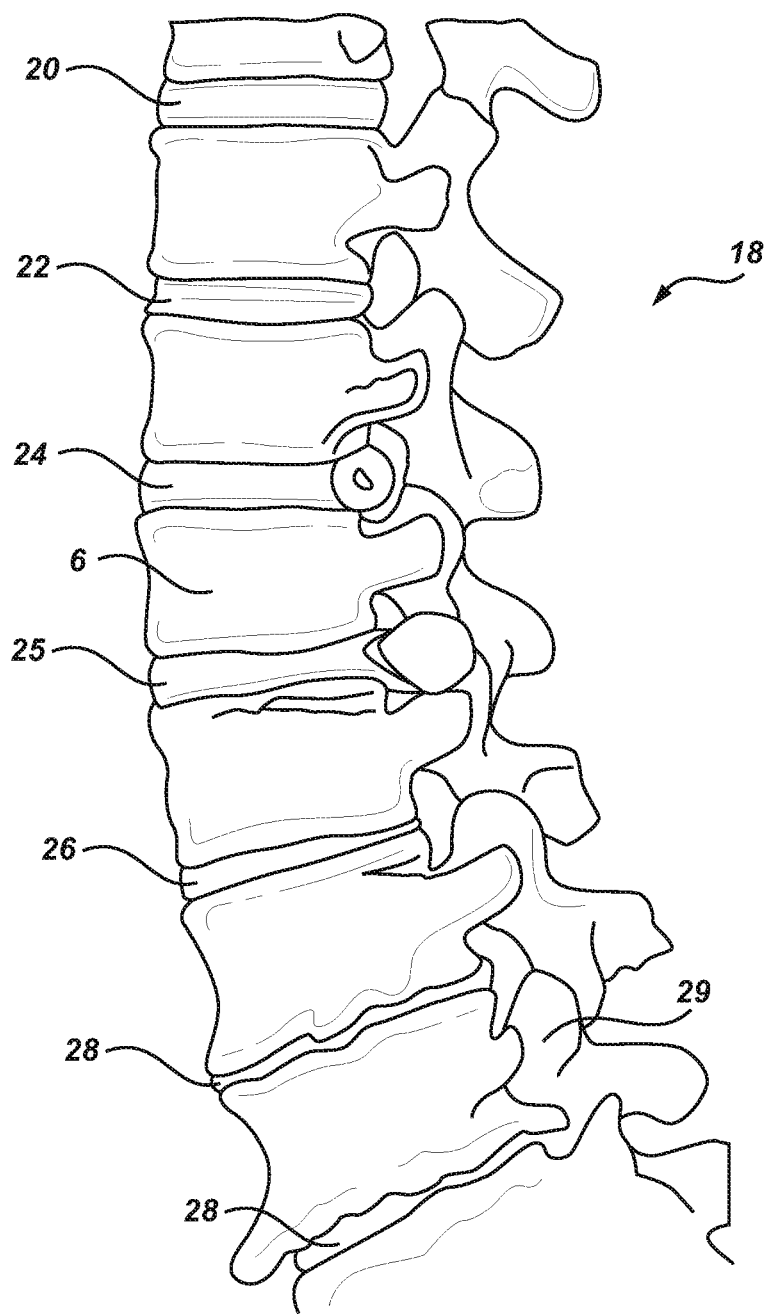
FIG. 3 is a segment of a spine illustrating various pathologies of intervertebral discs.
Figure 4:
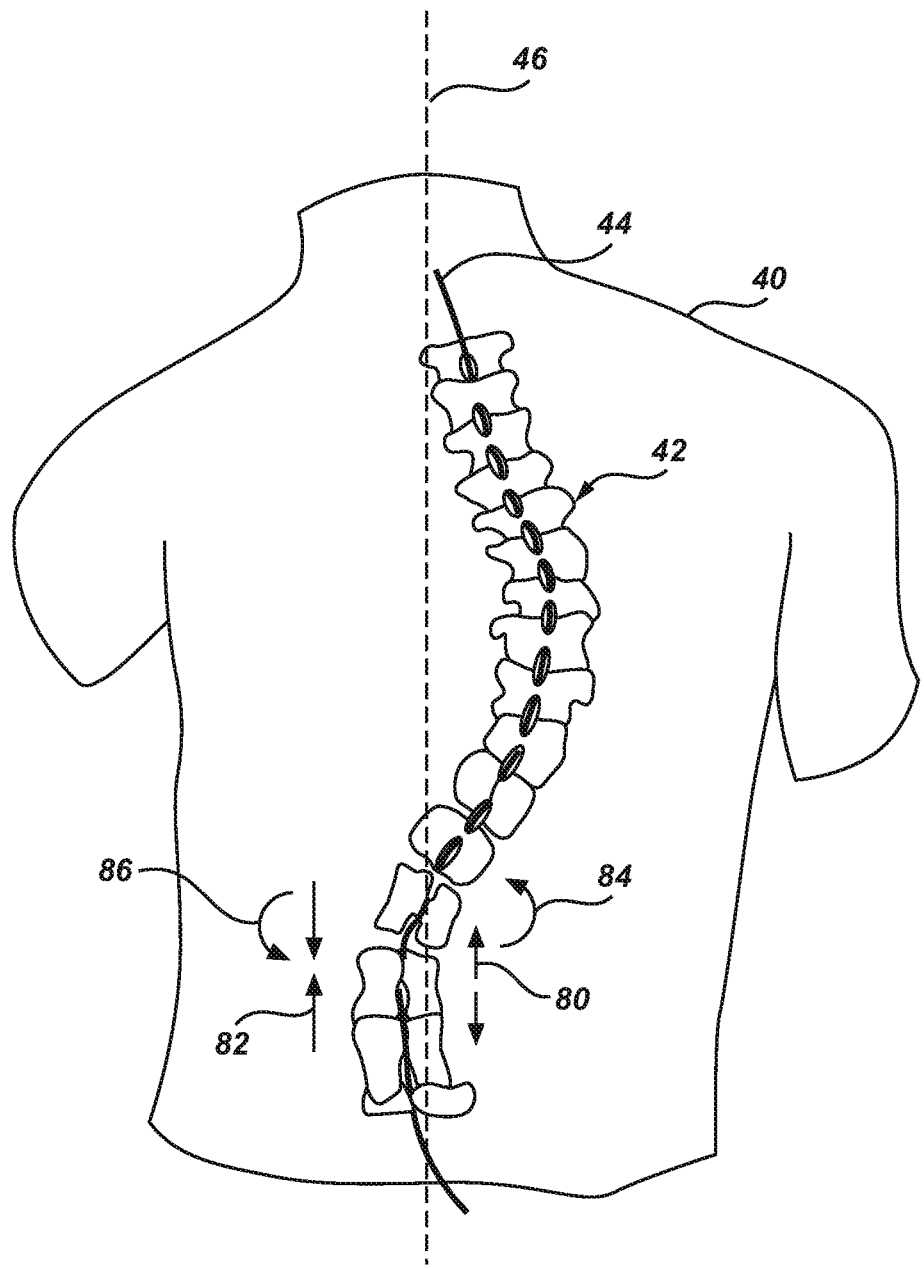
FIG. 4 is a scoliotic spine.
Figure 12:
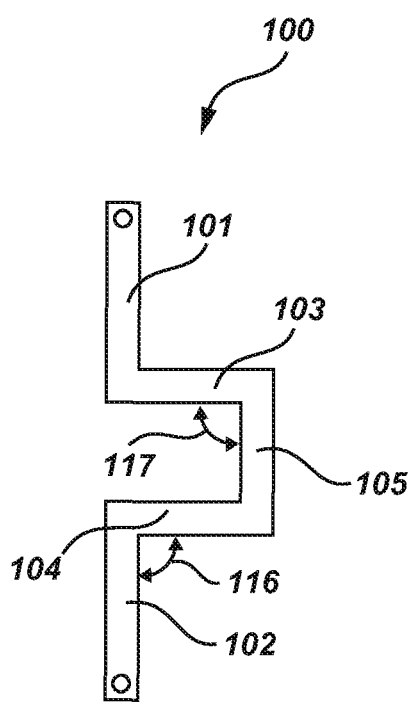
FIG. 12 is a posterior view of the spinal implant of FIG. 8 undergoing a torsional load.
Figure 13:
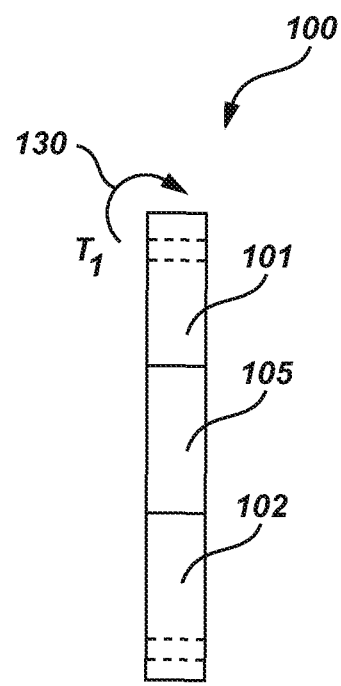
FIG. 13 is a lateral view of the spinal implant of FIG. 9 undergoing a torsional load.

Turning to FIGS. 12 and 13, these figures illustrate the spinal implants 100 from FIGS. 8 and 9 as they might appear during surgical implantation. As noted in the discussion of FIG. 9 above, the spinal implant 100 optionally is manufactured (or shaped, in the case of shape-memory materials like nitinol) to have a first geometry, which may include a first radius of curvature 121, the radius of curvature is about an axis orthogonal to the axis of the spinal column (e.g., axis 44 in FIG. 4). To implant the spinal implant 100, a surgeon could use a positioning tool that provides a torque 130 that causes the radius of curvature 121 to increase, potential to infinity, in the illustrated instance. In such a position, the surgeon can fix the spinal implants 100 to the patient's vertebrae (vertebrae 204 in FIGS. 10 and 11) with pedicle screws or other methods. Once the positioning tool is released and, consequently, torque 130 removed, the spinal implant 100 tends to return to its original, unstressed state and, in so doing, applies a torque 212 to the vertebrae 204 as illustrated in FIGS. 10 and 11.

FIGS. 14 and 15 illustrate the spinal implant 100 under a compressive force 142. This load could be caused by the normal action of gravity when implanted in a patient as the spinal implant 100 bears some of the compressive load. Alternatively or in addition to the load of gravity, such a force may occur as a result of lateral extension—i.e., the patient is leaning toward that side as a result of rotation 64 around the Y-axis 63 illustrated in FIG. 6. As FIG. 14 indicates, the third segment 103 and the fourth segment 104 deflect, causing a change in the first, second and fourth angles, 115, 117, and 116, respectively. The deflection of the segments 103 and 104 creates a torque that balances the compressive force 142.

In addition, a torque 140 can be applied to the spinal implant 100, a situation that might occur when the patient is leaning forward, causing flexion, i.e. a rotation around the X-axis 60 in the forward direction (flexion 61) in the spinal region in which the spinal implant 100 has been fixed. Such a movement would cause compression of the anterior region 207 of a diseased disc 206 as illustrated in FIG. 11. The spinal implant 100, by bending, applies a torque that would counteract, at least in part, the torque 142 caused by flexion. As one having skill in the art would understand, embodiments of the spinal implants 100 having a selected geometry such as that illustrated, would provide similar torque to balance and/or offset other forces incurred through flexion-extension, lateral extension/bending, and axial rotation.

A benefit of embodiments of the spinal implant are that it can be individually adjusted to a specific patient and that patient's pathologies, rather than relying on prior art devices that were manufactured for a predetermined subset of the population. The disadvantages of the latter approach are that it is rare that an individual patient's pathologies, by coincidence, are an exact match for a device. Thus, the patient must compromise, to a greater or lesser extent, on the performance and the relief that may be obtained through the use of some prior art devices.

Figure 6:
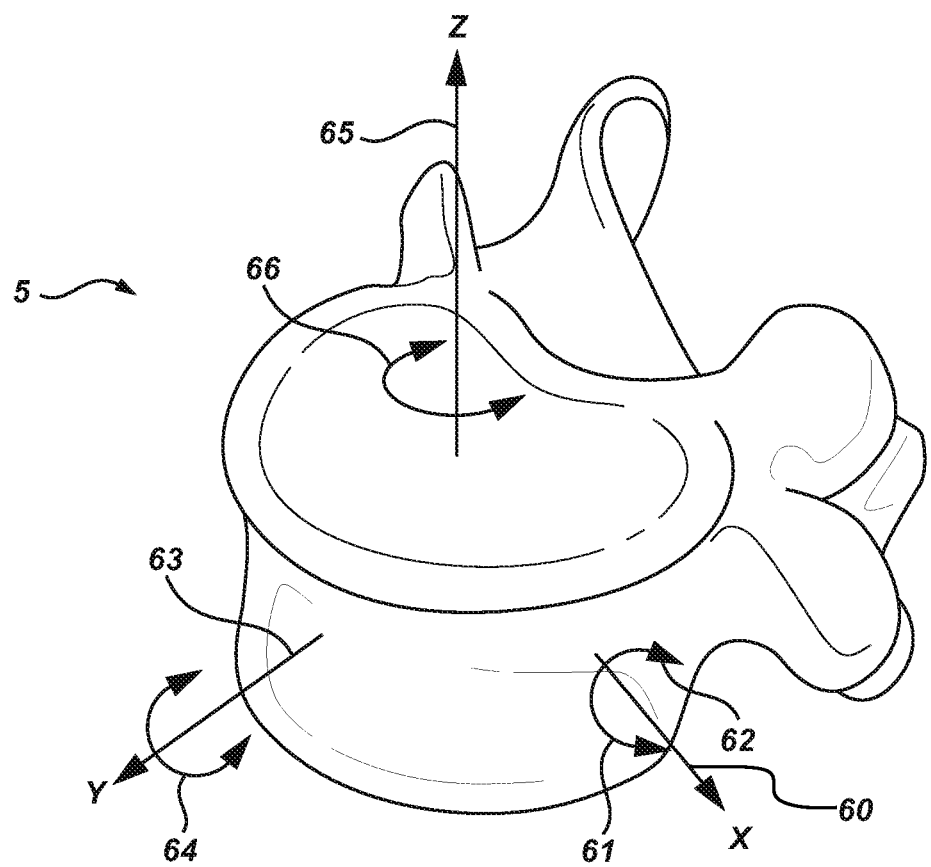
FIG. 6 illustrates the three axes of motion around which functional spine unit moves.
Figure 7:
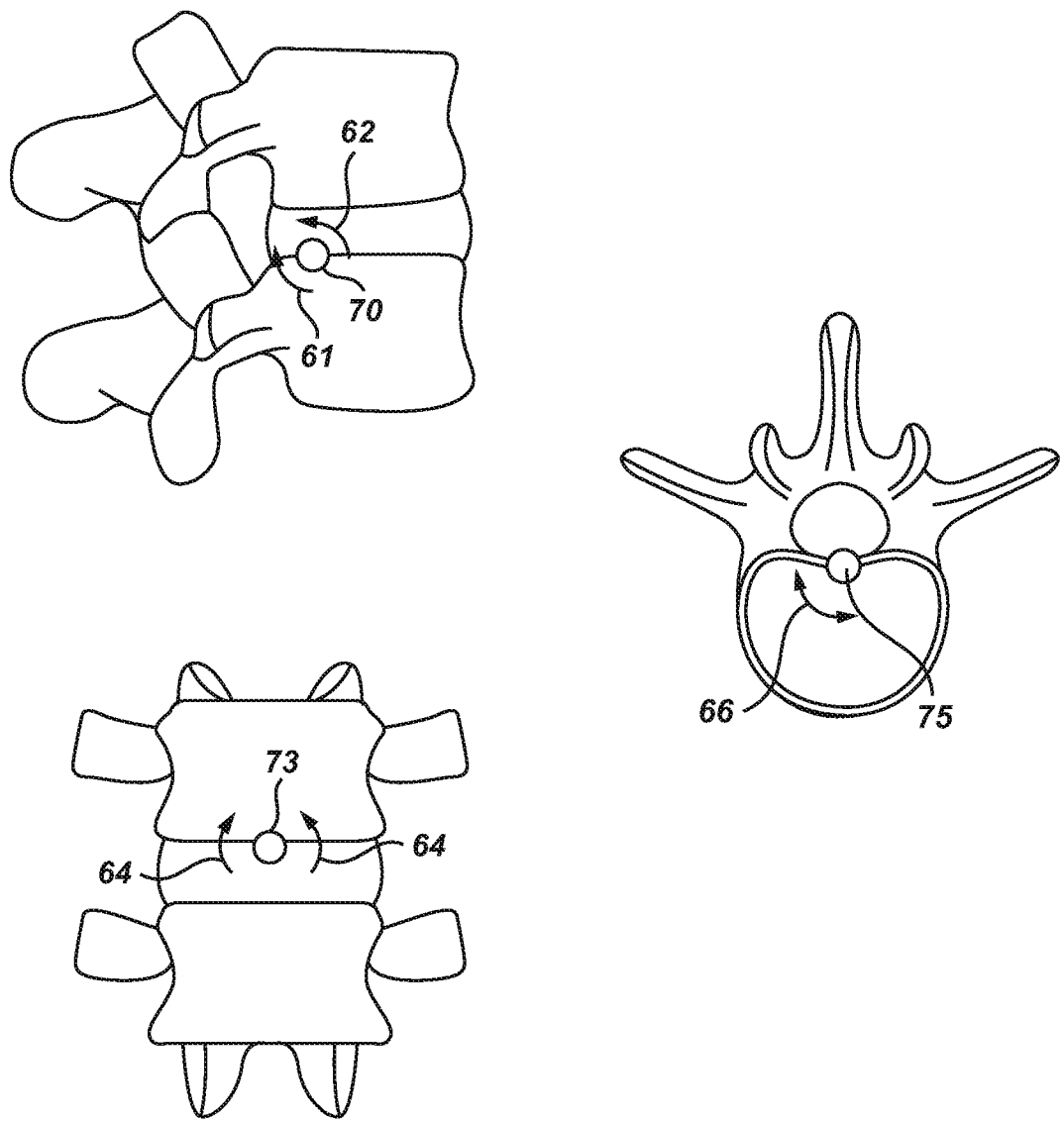
FIG. 7 illustrates the centers-of-motion of a functional spine unit.
Figure 16:
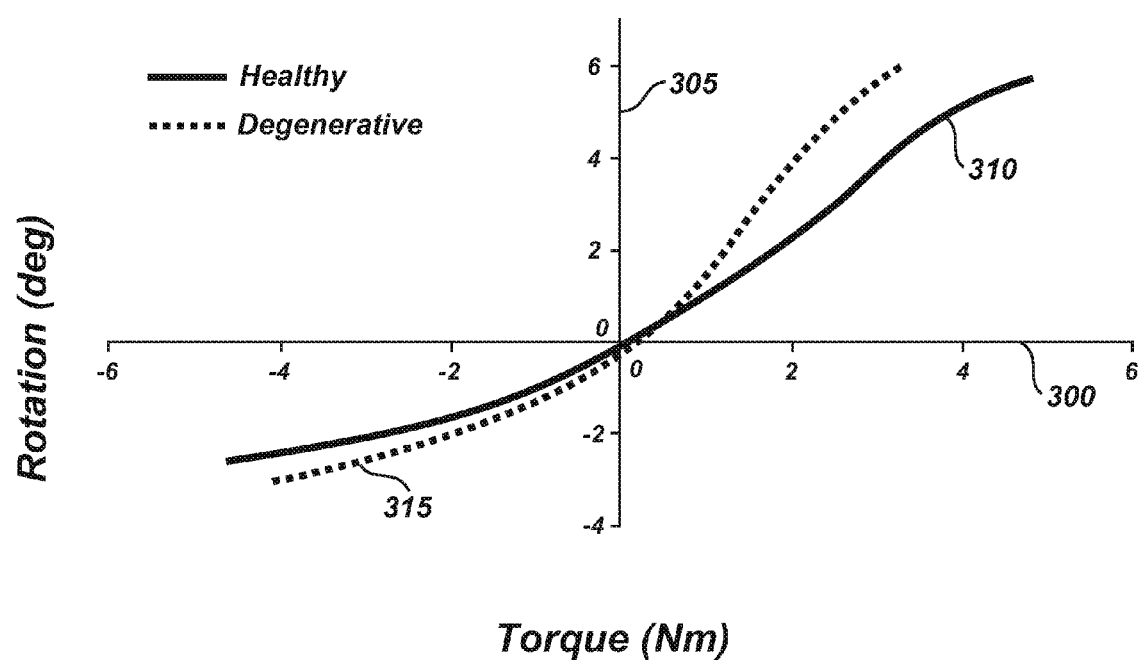
FIG. 16 is a graph of the rotation that occurs for a given torque for an exemplary healthy spine and an exemplary degenerative spine undergoing flexion and extension.
Figure 17:
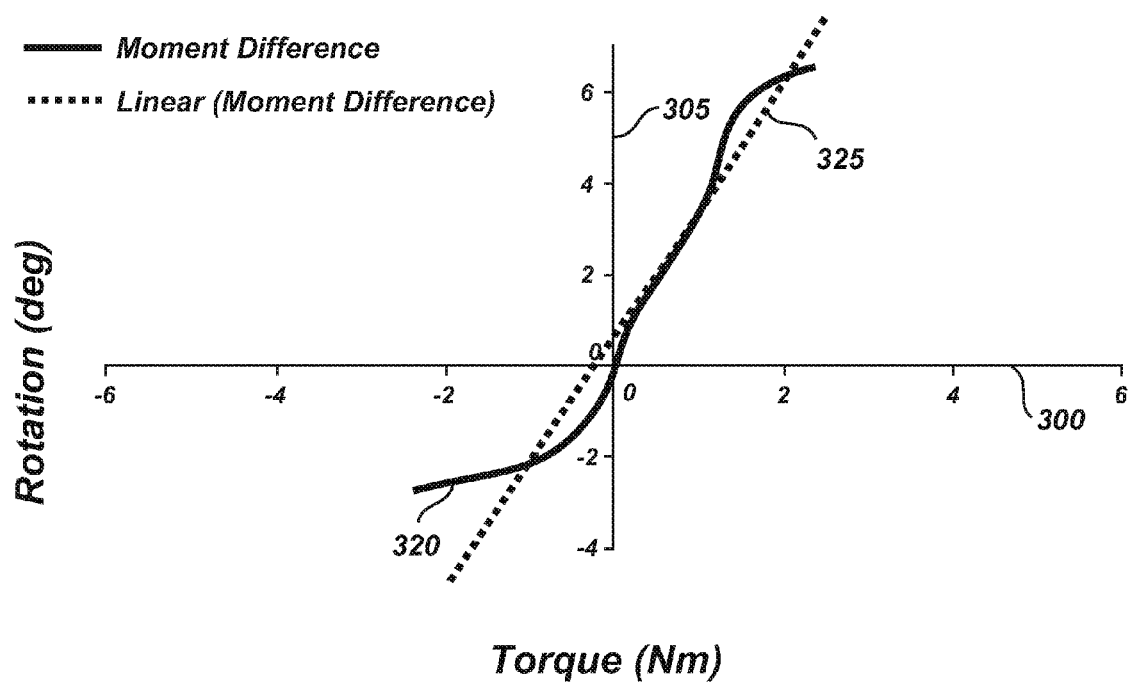
FIG. 17 is a graph of the moment difference between the response of the degenerative spine and the healthy spine graphed in FIG. 16 and a linear curve fit of the moment difference; and, FIG. 18 is a graph of the healthy spine of FIG. 16 and the resultant rotation that occurs for a given torque of the degenerative spine (shown in FIG. 16) that has had an embodiment of the spinal implant that has been adjusted to exhibit a torque response that is the negative slope of the linear curve fit shown in FIG. 17.
Figure 18:
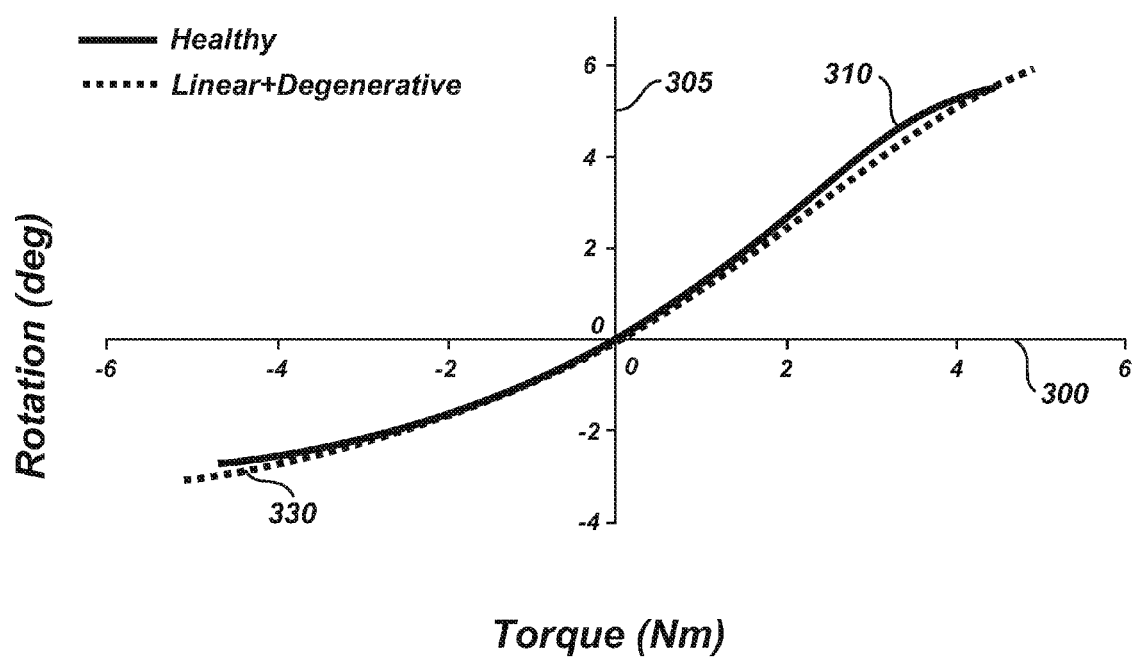

Referring to FIGS. 16-18, a process for selecting and adjusting a spinal implant to a patient's pathology will be discussed. FIG. 16 is a graph of the torque-rotation response of a healthy and a diseased or degenerative disc undergoing flexion and extension, i.e., rotation in flexion 61 and extension 62 around the X-axis 60 as illustrated in FIG. 6 and corresponding to bending or leaning over and bending or leaning backwards. The X-axis 300 of the graph is the torque measured in Newton·meters (Nm). The Y-axis 305 of the graph is a measurement of the range of motion in rotation in degrees. The solid (healthy) curve 310 is the response of a healthy functional spine unit which, for example, can include the disc 208 illustrated in FIG. 11. The dotted (degenerate) curve 315 is the response of a diseased or degenerative disc, such as disc 206 illustrated in FIG. 11. Qualitatively, FIG. 16 indicates that the diseased disc rotates more at lower torque than the healthy disc, indicating that there is a greater degree of laxity in the diseased disc, which may present as the disc bulging anteriorly and pressing against the spinal cord, causing pain, and/or other similar pathology. These measurements can be taken for the spine, as a whole, but, more preferably, the measurements are made at the vertebrae adjacent to the diseased disc. This is so because the torque-rotation response of the adjacent healthy vertebrae and discs should be the most similar to the response of the diseased disc when it was once healthy, a consideration since it is desired to restore the diseased disc to health.

Referring now to FIG. 17, this graph uses the same axes and scale as the graph in FIG. 16. In this instance, FIG. 17 plots the solid (moment difference) curve 320, which is the calculated difference in the response between the solid (healthy) curve 310 and the dotted (degenerate) curve 315 in FIG. 16. The dashed (linear) curve 325 is a linear curve fit of the solid (moment difference) curve 320.

A difference and improvement in the embodiments of the spinal implant disclosed herein is that the geometry of the spinal implant optionally uses this calculated moment difference as an input in the design process. The spinal implant 200 of FIGS. 10 and 11, for example, can be designed to have a radius of curvature 121 (illustrated in FIG. 9) that provides a desired and known torque response when implanted in the patient as discussed above. In this example, the spinal implant 200 would have a linear torque-rotation response in flexion-extension that has a slope that is the negative of the dashed (linear) curve 200.

FIG. 18 illustrates the reason for creating a spinal implant that relies, in part, on the moment difference between the healthy disc and the diseased disc. Again, the same axes and scale are used in FIG. 18 as in FIG. 16. In this graph, the original solid (healthy) curve 310 is plotted. Now, however, a spinal implant designed and adjusted for the patient's pathology, has been implanted as described above with respect to FIGS. 10 and 11. In other words, a spinal implant 200 is now supporting the diseased disc 206 and the adjacent vertebrae 204. As can be seen in FIG. 18, the spinal implant provides a desired stiffness, restoring the response of the dotted (degenerate) curve 315 to that of the dashed (linear and degenerate) curve 330 that is similar to the solid (healthy) curve 210. Qualitatively, it can be seen that with the spinal implant, the rotational response for a given torque is quite near that of the healthy disc. While this example is provided for flexion and extension, one having skill in the art would understand that similar measurements can be made for lateral extension and axial rotation so that the results can be used, in part, as an input into the geometry of the spinal implant and, therefore, to allow the spinal implant to accommodate and support the motion of the spine in the three axes as discussed above. In brief, embodiments of the spinal implant can be designed and adjusted, in part, pre-operatively for an individual patient's pathology. Embodiments of the spinal implant can restore, at least in part, a healthy torque-rotation signature to a diseased spine.

A further advantage of the above approach of measuring torque-rotation and similar data for use as an input is that it avoids a problem that appears in prior art devices. As briefly alluded to, many prior art devices have a limited range over which they function, typically force-displacement in compression and extension for the devices that commonly rely upon springs. These devices are not typically calibrated to an individual. As a result, it is not uncommon for these prior art devices to use an extension force to distract the diseased disc that is too large for a given individual, causing undue strain on the surrounding muscles and ligaments, which may result in undue pain. In severe cases, the pain this causes might result in the patient unduly limiting his or her range of motion, resulting in nutritional deficiencies and other problems associated with minimal or a lack of movement in the spine and the disc, which was the outcome to be avoided initially.

Embodiments of the spinal implant disclosed herein provide additional benefits, such as:

Treating scoliosis, kyphosis, lordosis, and/or similar pathologies: For example, with reference to FIG. 4 which illustrates a spine presenting with scoliosis, embodiments of the disclosed spinal implant can treat the scoliosis. This is done by using spinal implants that have different torque-rotation signatures from each other. That is, rather than using spinal implants 200 having the same torque-rotation signature as illustrated in FIG. 10, in the instance of scoliosis one of the spinal implants would have a different and, possibly, opposite, torque-rotation signature than the other. In addition, a prestressed force may be applied to one or both of the spinal implants so that they apply a force to one or both sides of the scoliotic spine. In other words, the torque and/or any force applied by the spinal implants would be unbalanced in order to counteract the curvature of the scoliotic spine. For example, in FIG. 4 an extensive force 82 can be applied on the right side of the lumbar area of the spine by one spinal implant, while on the left side another spinal implant could apply a compressive force on the left side of the lumbar area of the spine, tending to cause the lumbar spine to straighten. Alternatively, or in addition to, the unbalanced forces, torques 84 and 86 could be applied to the spine by the spinal implants. A similar strategy could be used to treat other conditions of the spine that present similar pathology to scoliosis, such as kyphosis, lordosis, and the like.

Figure 5:
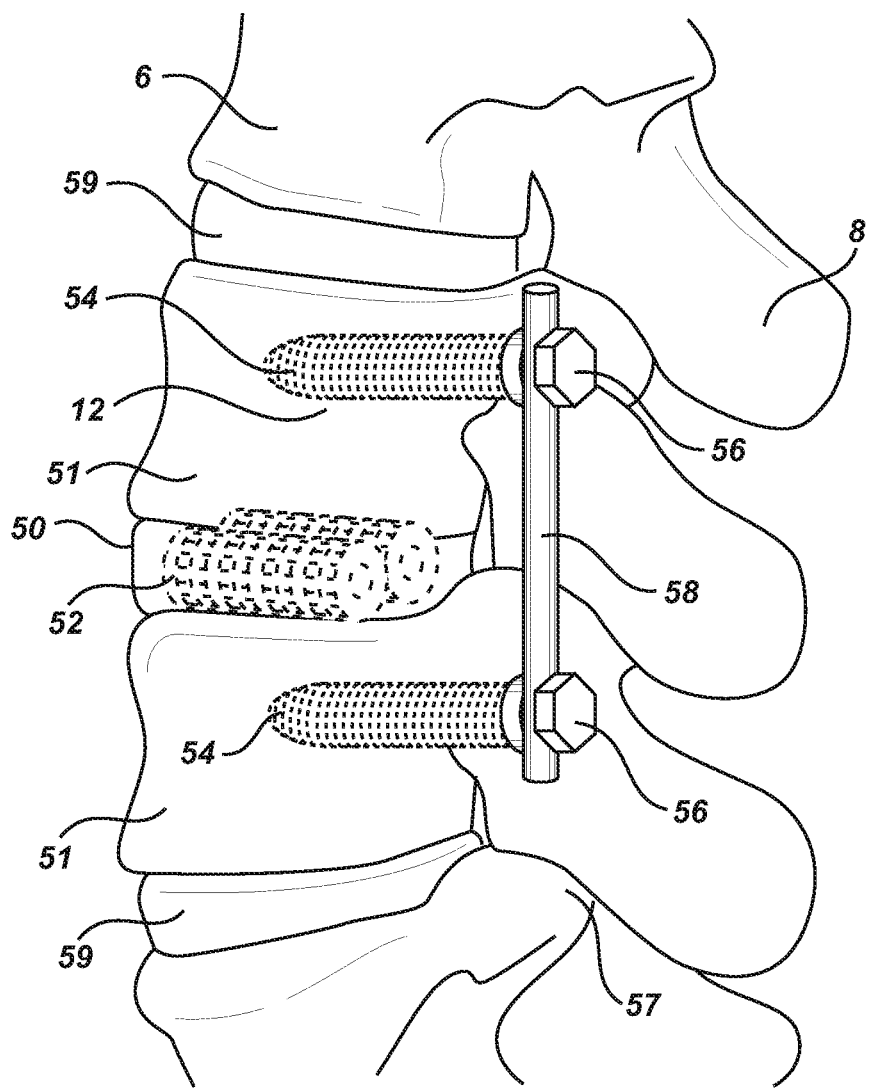
FIG. 5 is a prior art discectomy and spinal fusion.

Provide distraction of the vertebrae to allow healing of the diseased disc: As noted, a spinal implant can be prestressed to provide a torque and/or extensive force to distract, either anteriorly, posteriorly, or both, the portion the vertebrae adjacent to a diseased disc. In so doing, the spinal implants carry or bear a portion of the force normally borne by the diseased disc, as well as an additional force that static devices such as the prior art posterior support 58 in FIG. 5 do not carry. This arrangement allows sufficient support and space for the diseased disc to heal while still providing for sufficient moment that static prior art devices and procedures (such as spinal fusion) do not provide. In other words, embodiments of the spinal implant provide an opportunity for the diseased disc to heal, which may allow the spinal implants to eventually be removed.

Protect spinal cord and periphery nerves: The embodiments disclosed provide, in part, a measure of protection to the spinal cord and peripheral nerves from being impinged by bulging and/or herniated discs and/or parts of the skeletal structure and other parts of the anatomy afflicted with various pathologies as described above.

Limit range of motion and provide stiffness: The embodiments disclosed, as shown graphically in FIGS. 16-18, restore a measure of stiffness and limit the range of motion that might otherwise be causing pain, such as through muscles overexerting themselves to compensate for the laxity caused by a diseased disc. By limiting the range of motion, the strain on muscles and ligaments is reduced, thereby reducing risk of injury to those muscles. Further, laxity is reduced, thereby improving the structural stiffness (as opposed to the colloquial muscle stiffness caused by over-exertion) of the spine.

Kinetics similar to a healthy spine: Related to limiting the range of motion discussed above, the motion that embodiments of the spinal implant provide in the three axes discussed above regarding FIG. 6 is similar to that of a healthy spine. What this provides is that the patient's muscles and ligaments do not have to compensate for an unnatural motion of the spinal implant, unlike the case with prior art devices. In other words, the spinal implant provides more natural motion, which would encourage patients to move more with less attendant pain as their muscles would not be compensating or overworking for a prior art spinal implant that does not provide such natural motion around all three axes. In so doing, the movement provides further nutrition to the discs, increasing the likelihood that the discs will heal.

Kinematics similar to a healthy spine: Related to the kinetics are the natural kinematics of embodiments of the spinal implants. As discussed above, the centers-of-rotation for flexion-extension, lateral extension/bending, and axial rotation, are each located in different places. Prior art devices could not accommodate these separate centers-of-rotation around more than one axis, if even that, nor could they provide for the instantaneous or near instantaneous change in the location of the centers-of-motion as a spinal segment moves, nor could they provide for motion approximate the motion of a natural helical axis. Stated differently, the center-of-rotation of prior art devices often was in a different location than the natural center-of-rotation of the spine for a given movement. To compensate, patients with prior art devices suffered strain upon the spinal cord and peripheral nerves, muscle strain caused by the muscles overworking and compensating for the two different centers-of-rotation (that of the prior art device and that of the spine), ligament strain, and, consequently, pain. In contrast, embodiments of the present spinal implant provide centers-of-rotation in each of the three axes that is the same, or nearly the same, as a patient's natural centers-of-rotation for the spine. Thus, patients typically have less pain and, consequently, greater movement, to the benefit of the discs and the spine in general.

Adjust to the individual spine: As noted, embodiments of the spinal implant can be designed and/or selected preoperatively for an individual patient's torque-rotation response in order to provide implants that restores the diseased disc/spine to near healthy function. Related to this is the ability to prestress embodiments of the implant prior to, or even during, surgery to allow the surgeon to further individually tailor the torque-rotation response of the spinal implant to the individual patient as determined at the time.

Further, embodiments of the spinal implant are adjustable post-surgically. As noted, spinal implants made of bioabsorbable material will gradually degrade and, in the process, transfer ever greater portions of the force and torque once borne by the spinal implant back to the patient's spine as it heals. A further benefit of this is that these embodiments do not need to be then be surgically removed, reducing cost and risks to the patient. Alternatively, embodiments of the spinal implant can be made from shape-memory materials, such as nitinol. The use of shape memory materials allows the spinal implant to be configured in a second geometry or shape upon surgical implantation and then, upon application of some transformation parameter, such as heat, the spinal implant reverts to a first geometry or shape with different mechanical properties (such as stiffness and/or torque), thus allow a physician to subsequently alter the treatment of the patient without surgical intervention.

Reduced wear: As noted, embodiments of the spinal implant do not have moving components or components that rub against one another, thereby reducing or eliminating the generation of wear particles. Further, because embodiments of the spinal implant rely upon torsion and/or torsion beams rather than compression and extension that springs and other similar devices rely upon, reduces or eliminates the risk of the material from which the spinal implant is made suffers from fatigue and/or fatigue failure, thereby increasing the reliability of the spinal implant.

Thus, disclosed above, in addition to the embodiments of the spinal implant are methods of treating a spine with a spinal implant configured to provide motion in three axes; methods of treating a spine with a spinal implant that provides kinetics and kinematics similar to that of a functional spine; methods of treating pathologies that cause the spine to curve; methods of healing a diseased or degenerated disc; methods of adjusting a spinal implant without surgical intervention; methods of reducing the wear of a spinal implant; methods of providing a near healthy torque-rotation signature to a degenerate spine; and other methods as will be recognized by one of skill in the art.

As alluded to above, embodiments of the spinal implant are surgically implanted. While the spinal implants disclosed herein can be implanted using either an anterior, posterior, or lateral incision in the patient, a preferred method is to use a posterior incision. Further, it is preferred that a minimally invasive procedure be used, such as by laparoscopy in which only one or a few, small incisions are made and the surgery is conducted with laparoscopic tools. The methods include making an incision; providing an embodiment of the spinal implant disclosed herein; using a positioning tool to position the spinal implant and counter and prestress designed into the spinal implant; and fixing the spinal implant to two adjacent vertebrae. The surgical procedure does not require that the disc space be distracted extensively to install the spinal implant, thereby reducing the pain and recovery time endured by the patient. The method optionally includes implanting spinal implants with different characteristics, such as different prestressed torques, for treating pathologies such as scoliosis. Fixing the spinal implant to the vertebrae may be done by applying straps, applying biocompatible adhesives, installing pedicle screws, and the like, as known in the art.

Alternative methods and positions of placing the spinal implant include locating them on the anterior side of the spine rather than the posterior side. Spinal implants positioned to the anterior side can be reached through an incision in the patient's back and positioned between the transverse process of adjacent vertebral bodies or mechanically attached to the anterior portion of the vertebral body.

The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A spinal implant comprising:
   first, second, third, fourth and fifth contiguous segments, with one of a first, second, third or fourth angle of intersection being defined between the contiguous segments where the contiguous segments intersect;
   said plurality of contiguous segments configured to collectively apply a torque to a degenerate spinal segment in each of three orthogonal axes; and,
   at least one mounting connection configured to connect said spinal implant to a mounting mechanism, said mounting mechanism being configured to attach said spinal implant to said degenerate spinal segment.

2. The spinal implant of claim 1, wherein each of said first, second, third and fourth angle of intersection is between about 80 degrees and about 110 degrees.

3. The spinal implant of claim 1, wherein said implant is made from at least one of biocompatible plastics, polymers, metals, metal alloys, laminates, shape-memory materials, and bioabsorbable materials.

4. The spinal implant of claim 1, wherein said spinal implant includes a radius of curvature in an unimplanted state to provide said torque.

5. A spinal implant comprising:
   first, second, third, fourth and fifth contiguous segments, with one of a first, second, third or fourth angle of intersection being defined between the contiguous segments where the contiguous segments intersect, said plurality of contiguous segments configured to collectively apply a torque to a degenerate spinal segment in each of three orthogonal axes, said contiguous segments configured to collectively provide said degenerative spinal segment a range of motion around each axis approximating a range of motion of a healthy spinal segment around each axis; and,
   at least one mounting connection configured to connect said spinal implant to a mounting mechanism, said mounting mechanism being configured to attach said spinal implant to said degenerate spinal segment.

6. The spinal implant of claim 5, wherein each of said first, second, third and fourth angle of intersection is between about 80 degrees and about 110 degrees.

7. The spinal implant of claim 5, wherein said implant is made from at least one of biocompatible plastics, polymers, metals, metal alloys, laminates, shape-memory materials, and bioabsorbable materials.

8. The spinal implant of claim 5, wherein said spinal implant includes a radius of curvature in an unimplanted state to provide said torque.

9. A spinal implant comprising:
   first, second, third, fourth and fifth contiguous segments, with one of a first, second, third or fourth angle of intersection being defined between the contiguous segments where the contiguous segments intersect, said contiguous segments configured to collectively apply a torque to a degenerate spinal segment in each of three orthogonal axes, said contiguous segments configured to provide said degenerate spinal segment a center-of-rotation around each axis proximate a center-of-rotation of a healthy spinal segment around each axis; and,
   at least one mounting connection configured to connect said spinal implant to a mounting mechanism, said mounting mechanism being configured to attach said spinal implant to said degenerate spinal segment.

10. The spinal implant of claim 9, wherein each of said first, second, third and fourth angle of intersection is between about 80 degrees and about 110 degrees.

11. The spinal implant of claim 9, wherein said implant is made from at least one of biocompatible plastics, polymers, metals, metal alloys, laminates, shape-memory materials, and bioabsorbable materials.

12. The spinal implant of claim 9, wherein said spinal implant includes a radius of curvature in an unimplanted state to provide said torque.

13. A spinal implant comprising:
    first, second, third, fourth and fifth contiguous segments, with one of a first, second, third or fourth angle of intersection being defined between the contiguous segments where the contiguous segments intersect, said contiguous segments configured to collectively apply a torque to a degenerate spinal segment in each of three orthogonal axes; and,
    at least one mounting connection configured to connect said spinal implant to a mounting mechanism, said mounting mechanism being configured to attach said spinal implant to said degenerate spinal segment.

14. The spinal implant of claim 13, wherein each of first, second, third and fourth angles are from about 80 degrees to about 110 degrees.

15. The spinal implant of claim 13, wherein said implant is made from at least one of biocompatible plastics, polymers, metals, metal alloys, laminates, shape-memory materials, and bioabsorbable materials.

16. The spinal implant of claim 13, wherein said spinal implant includes a radius of curvature in an unimplanted state to provide said torque.

17. A method of healing a degenerate spinal segment comprising:
    obtaining at least one spinal implant configured to apply a torque to at least one vertebra adjacent to a degenerate intervertebral disc, said spinal implant including:
    first, second, third, fourth and fifth contiguous segments, with one of a first, second, third or fourth angle of intersection being defined between the contiguous segments where the contiguous segments intersect, said segments configured to collectively apply a torque to at least one vertebra of a patient in each of three orthogonal axes;
    at least one mounting connection configured to connect said spinal implant to a mounting mechanism, said mounting mechanism being configured to attach said spinal implant to said vertebra; and,
    implanting said spinal implant to said vertebra such that said torque distracts said vertebra from said degenerate intervertebral disc.

18. The method of claim 17, wherein said spinal implant includes a radius of curvature to in an unimplanted state to provide said torque.

19. The method of claim 17, wherein said torque distracts at least one of an anterior portion and a posterior portion of said vertebra from said degenerate intervertebral disc.

20. A method of making a spinal implant comprising:
    forming a spinal implant from at least one of biocompatible plastics, polymers, metals, metal alloys, laminates, shape-memory materials, and bioabsorbable materials, said spinal implant configured to apply a torque to a degenerate spinal segment in each of three orthogonal axes, said spinal implant including:
    first, second, third, fourth and fifth contiguous segments, with one of a first, second, third or fourth angle of intersection being defined between the contiguous segments where the contiguous segments intersect, said contiguous segments configured to collectively apply a torque to said degenerate spinal segment;
    at least one mounting connection configured to connect said spinal implant to a mounting mechanism, said mounting mechanism being configured to attach said spinal implant to said degenerate spinal segment.

21. The method of claim 20 further comprising forming said plurality of contiguous segments from of a single piece of material.

22. The method of claim 21, wherein forming further comprises at least one of laminating, molding, pressing, stamping, milling.

23. The method of claim 20, wherein said forming said spinal implant includes forming said spinal implant with a radius of curvature selected to apply said torque.

24. The method of claim 20, further comprising:
    forming said spinal implant of said shape-memory material in a first configuration having a first known torque response; and,
    manipulating said spinal implant into a second configuration having a second known torque response.

25. The method of claim 24, wherein said first configuration has a first radius of curvature and said second configuration has a second radius of curvature different from said first radius of curvature.

26. A method of adjusting a spinal implant comprising:
    accessing at least one implanted spinal implant configured to apply a torque to a degenerate spinal segment, said spinal implant including:
    first, second, third, fourth and fifth contiguous segments, with one of a first, second, third or fourth angle of intersection being defined between the contiguous segments where the contiguous segments intersect, said contiguous segments configured to collectively apply a torque to degenerate spinal segment in each of three orthogonal axes;
    at least one mounting connection configured to connect said spinal implant to a mounting mechanism, said mounting mechanism being configured to attach said spinal implant to said degenerate spinal segment;

adjusting said spinal implant post-operatively to modify said torque.

27. The method of claim 26, wherein providing said spinal implant further comprises:
provided a spinal implant made of a shape-memory material having a first configuration having a first known torque response and a second configuration having a second known torque response;
implanting said spinal implant when said spinal implant is in its second configuration; and,
applying a parameter to said spinal implant, said parameter being selected to cause said spinal implant to change from its second configuration to its first configuration.

28. The method of claim 27, wherein in applying said parameter comprises applying heat to said spinal implant.

29. The method of claim 27, wherein providing said spinal implant further comprises providing a spinal implant made of a bioabsorbable material, thereby causing said torque to be reduced as said spinal implant is absorbed.

* * * * *